(12) United States Patent
Nofsinger

(10) Patent No.: US 9,700,259 B1
(45) Date of Patent: *Jul. 11, 2017

(54) RAPID CUSTOM INTRA-ARTICULAR LIGAMENT RECONSTRUCTION GUIDE

(71) Applicant: Charles Nofsinger, Land O' Lakes, FL (US)

(72) Inventor: Charles Nofsinger, Land O' Lakes, FL (US)

(73) Assignee: University of South Florida, Tampa, FL (US)

( * ) Notice: Subject to any disclaimer, the term of this patent is extended or adjusted under 35 U.S.C. 154(b) by 556 days.

This patent is subject to a terminal disclaimer.

(21) Appl. No.: 14/287,987

(22) Filed: May 27, 2014

Related U.S. Application Data

(63) Continuation-in-part of application No. 12/537,779, filed on Aug. 7, 2009, now Pat. No. 8,808,301.

(60) Provisional application No. 61/086,949, filed on Aug. 7, 2008.

(51) Int. Cl.
*A61B 17/58* (2006.01)
*A61B 17/60* (2006.01)
*A61F 2/00* (2006.01)
*A61B 5/00* (2006.01)

(52) U.S. Cl.
CPC .......... *A61B 5/4533* (2013.01); *A61B 5/4528* (2013.01); *A61B 2576/02* (2013.01)

(58) Field of Classification Search
CPC . A61B 17/17; A61B 17/1714; A61B 17/1739; A61B 17/1764; A61B 17/1778; A61B 2017/568; A61B 2034/108; A61B 5/4528; A61B 5/4533; A61F 2/08; A61F 2/0811

USPC .................. 606/86 R–89 R, 96–98, 102, 104
See application file for complete search history.

(56) References Cited

U.S. PATENT DOCUMENTS

| | | |
|---|---|---|
| 3,545,008 A | 12/1970 | Bader, Jr. |
| 3,882,551 A | 5/1975 | Helmer et al. |
| 3,896,500 A | 7/1975 | Rambert et al. |
| 3,953,896 A | 5/1976 | Treace |
| 3,973,277 A | 8/1976 | Semple et al. |
| 4,246,660 A | 1/1981 | Wevers |
| 4,744,353 A | 5/1988 | McFarland |
| 5,092,887 A | 3/1992 | Gendler |
| 5,562,669 A | 10/1996 | McGuire |
| 6,533,737 B1 | 3/2003 | Brosseau et al. |

(Continued)

OTHER PUBLICATIONS

Reider et al., The Bankart procedure modified by the use of prolene pull-out sutures, J Bone Joint Surg. Am., 1982, vol. 64, pp. 628-629.

(Continued)

*Primary Examiner* — Si Ming Ku
(74) *Attorney, Agent, or Firm* — Nicholas Pfeifer; Smith & Hopen, P.A.

(57) ABSTRACT

The present invention is a method of creating custom surgical guides based on the patient's unique anatomy that can be quickly and accurately applied intra-operatively without navigation are disclosed. The device is created using preoperative MRI images and uniquely conforms to the bone in the region of the desired tunnel. The images are filtered and used to generate computerized three dimensional models of surgical guides that conform to the patient's anatomy. The surgical guides can be introduced through a portal and applied to the bone denuded of soft tissue.

20 Claims, 9 Drawing Sheets

(56) References Cited

U.S. PATENT DOCUMENTS

2005/0101966 A1   5/2005  Lavallee
2007/0185498 A2   8/2007  Lavallee

OTHER PUBLICATIONS

Miller et al., Cruciate Ligament Graft Intra-articular Distances, Arthroscopy: The Journal of Arthroscopic and Related Surgery, Jun. 1997, vol. 13, No. 3, pp. 291-295.

A

B

A

B

A

B

RAPID CUSTOM INTRA-ARTICULAR LIGAMENT RECONSTRUCTION GUIDE

CROSS REFERENCE TO RELATED APPLICATION

This application is a continuation-in-part and claims priority to U.S. Nonprovisional patent application Ser. No. 12/537,779, entitled "Rapid Custom Intra-Articular Ligament Reconstruction Guide", filed on Aug. 7, 2009, which in turn claims priority to U.S. Provisional Patent Application No. 61/086,949, entitled "Rapid Custom Intra-Articular Ligament Reconstruction Guide", filed on Aug. 7, 2008.

FIELD OF INVENTION

This invention relates to a method of generating custom surgical guides. Specifically, the invention entails using a patient's medical images to develop custom surgical guides.

BACKGROUND OF THE INVENTION

Joint damage, such as dislocation or ligament tearing, is often a result of connective tissue damage, weakening or breaking the connection between the soft tissue and bone. Resultant weakening can lead to recurring dislocation or reduced joint integrity.

For joint surgery, such as anterior cruciate ligament reconstruction surgery, a bone tunnel is formed in each of two bones of the joint. In knee surgery, these are the femur and the tibia. Preferably, the bone tunnel is formed by drilling a core out through the bone such that the core might be used to form the bone plug in the composite graft. The bone plugs are machined to form two longitudinal substantially parallel grooves opposite one another. At least one ligament replacement, such as a semitendinosus tendon, and/or gracilis, is extended between both of two bone plugs along the parallel grooves in each plug. The ligament replacement is attached to the two bone plugs. Each bone plug is inserted into one of the bone tunnels and secured therein by an interference screw. The use of the bone-tendon-bone composite graft of the invention results in a reconstructed cruciate ligament, also, in accordance with an embodiment the present invention.

Although the lengths of the anterior and posterior cruciate ligaments have been well characterized in the literature, there are few studies of the actual length of these ligaments or the size needed for reconstruction grafts. Current placement of ligament reconstruction surgery is based on current recommendations, and the intra-articular graft length less than published values for the ligaments themselves, and that the patella tendon graft is of adequate length to be used for reconstruction of these ligaments. (Miller, L., et al., Cruciate ligament graft intra-articular distances, Arthroscopy: J of Arthro & Related Surg, 13:3, 291-295).

Intra-articular entry points for ligament reconcontruction was traditionally performed using landmark recognition, requiring a constant anatomical landmark, such as the intercondylar notch, to orient placement of a guide. Many times, the placement of intra-articular ligament reconstruction tunnels was too far anterior, resulting in small surgical tunnels, uneven bone plug reconstruction, and delayed graft failure. Alternatively or in conjection with landmark recognition, tunnel placement is based on computer navigation. However, landmark recognition and computer navigation assume similar patient anatomy with respect to the patient's bones and ligaments. Multiple published studies show current reconcontruction technology has an inaccurate placement and therefore non-anatomic restoration of knee kinematics. Accurate ligament attachment shows improved joint kinematics. However, studies of current technologies indicate there exists a high probability for inaccurate placement during reconstruction, and therefore non-anatomic restoration of the joint. Accordingly, there exists a need for an improved ligament reconstruction guide to allow better anatomical placement during reconstruction surgery.

However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The present invention is a novel method of creating a custom surgical guide based on a patients unique anatomy that can be quickly and accurately applied intra-operatively without navigation. The guide is created from preoperative MRI and uniquely conforms to the bone in the region of the desired tunnel. The guide can be introduced through a portal and applied to the bone denuded of soft tissue. Computer-assisted surgical systems have been used to assist doctors during a surgical procedure, from displaying status and data on the patient's physical condition to allowing displaying computer generated models of the anatomical structures of interest to help the surgeon visualize the surgical procedure being performed, as described in U.S. Pat. No. 6,533,737 to Brosseau et al. The surgical guide includes a body having a first end, a second end, a contacting surface, a top surface, and a tooling guide disposed near the second end and at the ligament attachment point. The first end is adapted to fit in an interstitial space between the bones of the joint and the contacting surface is inversely contoured to the shape of the patient's joint anatomy.

The tooling guide can be any tool guide known in the art, such as guide cut out, drill guide, groove tracks. Examples of tools that may be used with the guide include awl, drill, osteotome, dental hatchet, burr, and coring reamer. The guide is useful in any joint surgery and has a face that is inversely correlated with the contours of the at least one anatomical bone structure, such as the epiphysis of the tibia and the epiphysis of the fibula. Of particular note, the guide is useful for ligament reconstruction, such as anterior cruciate ligament (ACL), medial cruciate ligament (MCL) reconstruction with natureal, cavadaric, or artificial ligament.

The method of manufacturing the surgical guide includes collecting at least one image of the joint requiring surgery using an image slice thickness of 0.499998 mm and patient image orientation of RAX—axially oriented in the scanner. These images are used to locate the ligament attachment point and generate a model of the joint. The model includes the attachment point so that the surgical guide can be manufactured with a tooling guide in perfect alignment with the ligament attachment point. The location of the tooling guide is based on the surgery. For example, in ligament surgery, the location is selected such that a coring hole will allow for an anatomically equivalent reconstruction. The surgical guide is then constructed. The tooling guide is also prepared, such that the tooling guide is disposed in the pre-determined location. Exemplary tooling guides include a guide cut out, drill guide, and groove tracks.

Imaging useful in the creating of the surgical guide include magnetic resonance imaging (MRI), nuclear magnetic resonance imaging (NMRI), computed axial tomography (CAT or CT scan) scan, ultrasound, fluoroscopy, x-ray, tomodensimetric (TDM), positron emission tomography (PET), and combinations thereof. In specific embodiments, image is an MRI image acquired using a magnetic field strength of 3 tesla. The image is optionally collected at an image resolution of 512 pixels by 512 pixels and the pixel size being 0.4688 mm.

In specific embodiments of the invention, the at least one image is processed. For example, at least one mask may be generated on the at least one medical image. In some embodiments, the mask is generated on top of the pixels within the contrast range of 0 to 800, 1250 to 4000, or both. Further, the at least one mask is processed to remove image artifacts. The ligament is removed from the image and the cortical bone representing the ligament attachment point remains. Optionally, the contours of the two bones from the image data are extracted from the image data and a reverse template of the bone contours is created. In specific embodiments of this, the image data is extracted using a Boolean extraction to create the reverse of the bone. The model of the ligament joint may be transferred to a three dimensional printer to generate a prototype.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
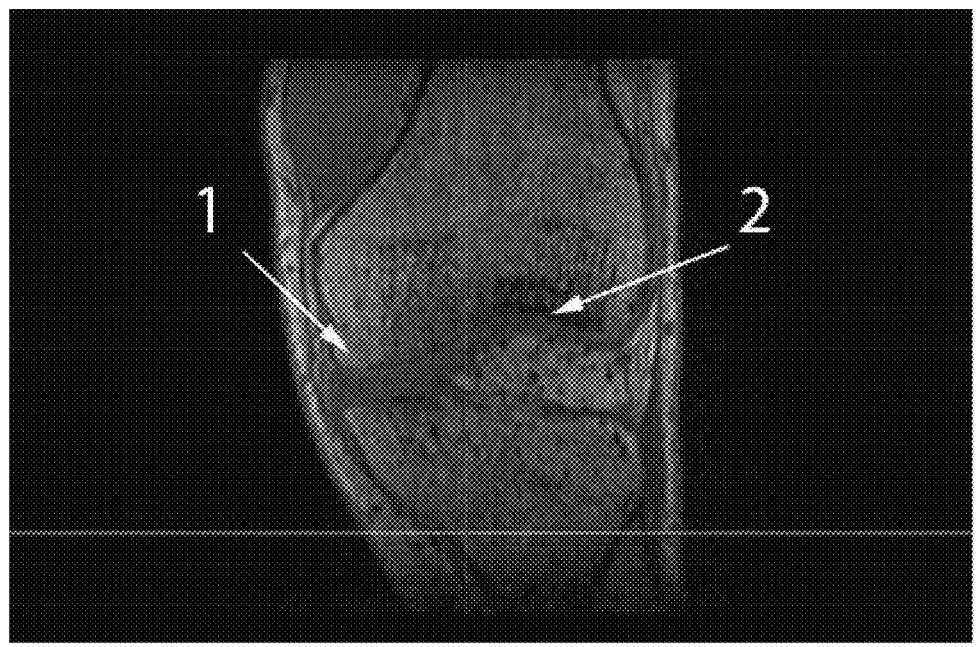
FIG. 1 depicts an image stack of 3D LAVA MRI images.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention is a method of designing and manufacturing a custom intra-articular ligament reconstruction guide. The custom surgical guide is designed to register using the epiphysis or articulation of the joint where the bones contact and allow for easy identification and location of the predetermined surgical site. The guide is useful in any joint surgery. Of particular note, the present invention is useful for ligament reconstruction, such as anterior cruciate ligament (ACL), medial cruciate ligament (MCL), and glenohumeral reconstruction with natureal, cavadaric, or artificial ligament. For the purposes of illustration, the utilization of the guide is described in an example as provided herein for a replacement of the Anterior Cruciate Ligament (ACL) of the knee by an artificial ligament.

As used herein, "artifact" refers to an artificial or distorted image present on a diagnostic image which is caused by an instrument, including the imaging device, procedure, or other form of intervention occurring during the imaging procedure. Artifacts include data that is not compact bone, such as other tissue with similar reaction to the imaging technique employed.

As used herein, "image" means the data that represents the spatial layout of anatomical or functional features of a patient, which may or may not be actually represented in visible, graphical form, including image data residing in a computer memory, as well as an image appearing on a computer screen. Non-limiting examples of images include an MRI image, a PET image, CAT image, ultrasound image, and the like. When using time sequence methods, such as ultrasound, as a data acquisition method, an "image" refers to one particular "frame" in the series that is appropriate for processing at that time.

As used herein, "imaging", "radiometric imaging", or "imaging modality" refers to at least one method or mechanism by which a diagnostic image of a joint is obtained. Imaging comprises use of at least one imaging method which, when performed to a subject, permits a diagnostic image of a part of the subject, including without limiting the invention, the use of static magnetic fields produced via radiofrequency pulse, x-ray radiation, or administration of a chemical entity that alters an anatomical structure allow for diagnostic image. Non-limiting examples include magnetic resonance imaging (MRI), nuclear magnetic resonance imaging (NMRI), computed axial tomography (CAT or CT scan) scan, ultrasound, fluoroscopy, x-ray, tomodensimetric (TDM), positron emission tomography (PET), and combinations thereof.

As used herein, "ligament" means a band of fibrous connective tissue composed of collagen fibers. The ligaments are connective tissue connecting bones to other bones to form a joint. Capsular ligaments surround synovial joints and act as mechanical reinforcements whereas extra-capsular ligaments join bones together and provide joint stability. "Natural ligament" means a ligament collected from a living organisms, such as autologous and allergenic sources. Other ligament sources include cadavaric and artificial ligaments. Cadavaric ligaments are ligaments collected from cadavers. Artificial ligaments are non-ligament material, and include without limiting the invention, elastomeric cords, elastomeric silicone materials and fabrics, ultra-high molecular weight polymers, like polyethylene, and demineralized bone. Nonlimiting examples of artifical ligaments may be found in Treace, U.S. Pat. No. 3,953,896; Rambert, et al., U.S. Pat. No. 3,896,500; Helmer, et al. U.S. Pat. No. 3,882,551; Semple, et al. U.S. Pat. No. 3,973,277; Bader, U.S. Pat. No. 3,545,008; Wevers, et al., U.S. Pat. No. 4,246,660; and Gendler, U.S. Pat. No. 5,092,887.

The method and process of the present invention includes collecting a radiometric image of a patient's joint. The image is preferably accomplished using MRI and Signa HDx 3.0T™ (General Electric Healthcare, Little Chalfont, Buckinghamshire, UK) with an image slice thickness of 0.499998 mm and patient image orientation of RAX. An MRI image stack is acquired, preferably by using 3D LAVA (General Electric Healthcare, Little Chalfont, Buckinghamshire, UK) settings and a magnetic field strength of 3 tesla. Additionally, the images are preferably collected at an image resolution of 512 pixels by 512 pixels and the pixel size being 0.4688 mm.

The collected MRI image stack is then segmented to reveal the ligament attachment point(s). Segmentation is achieved through applying one or more masks to the images or image stack. The process is preferably carried out by importing the images into Mimics, version 12.01 (Materialise NV, Leuven, Belgium), imaging software, which allows the user to generate three-dimensional models from medical data, view images with the full contrast levels of the MRI image stack, and allow the user visual access to all data present in the image stack. Masks are generated on top of each individual medical image, with preferably two different masks formed on each image.

Figure 2:
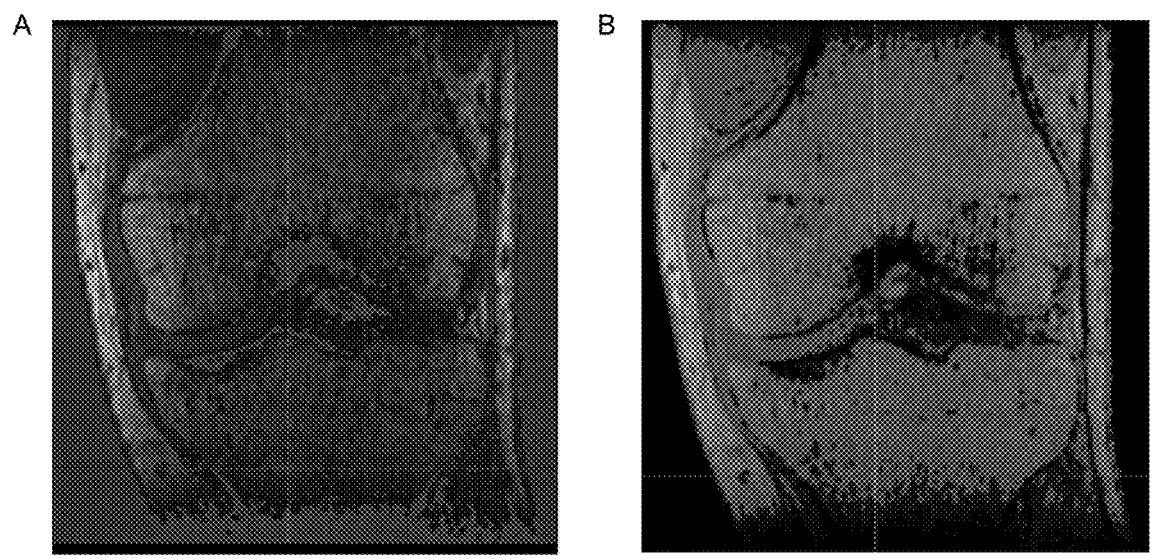
FIGS. 2(a) and (b) depict masks of the medical image pixels. In 2(a) the image highlights the pixels of the compact bone and in 2(b) the image highlights the pixels of spongy bone.

The first mask filters the pixels that are within the range of 0 to 800 and eliminates the rest, as seen in FIG. 2(a). These pixels contain a representation of the compact bone in the image stack. Additionally, artifacts are also collected and extracted from the mask. Similarly, the second mask is created from pixels in the contrast range of 1250 to 4000, seen in FIG. 2(b). These pixels contain data of the spongy bone and define the edges of bone. The second mask also contains artifacts and the mask is cleaned, leaving only the bone. The use of two different masks is preferable due to the manner of MRI image stack display. Volume averaging occurs across voxels of MRI space, so the different masks combine to better delineate edge data. As shown in FIG. 1, some edges are well defined by a dark edge 2 while others by a light edge 1. The second mask contrasts with the first mask to reveal the attachment point geometry.

Figure 3:
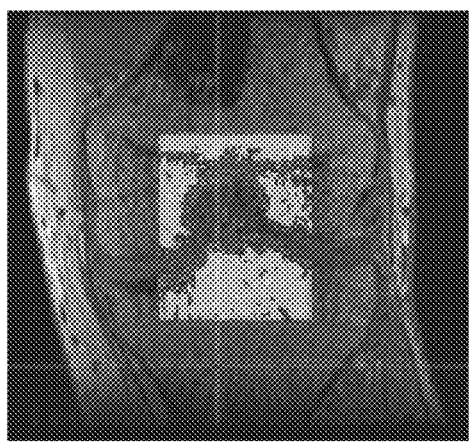
FIGS. 3(a) and (b) depict the masks after data processing to remove artifacts. In 3(a) the two masks from FIG. 2 are overlaid on each other after cropping, and then in 3(b) the two masks are merged and filled.
Figure 3:
Figure 4:
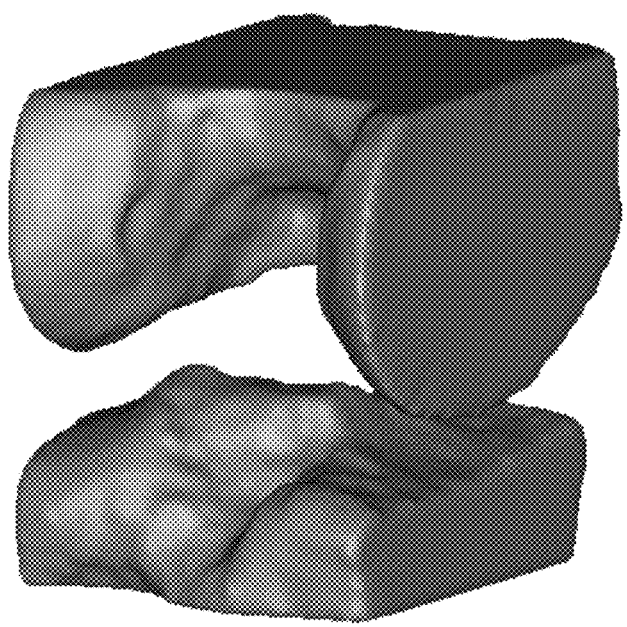
FIGS. 4(a) and (b) depict a computer generated mask of the bone. In 4(a) a computer generated mask is created and used in 4(b) to generate a reverse image of the space of the knee.
Figure 4:
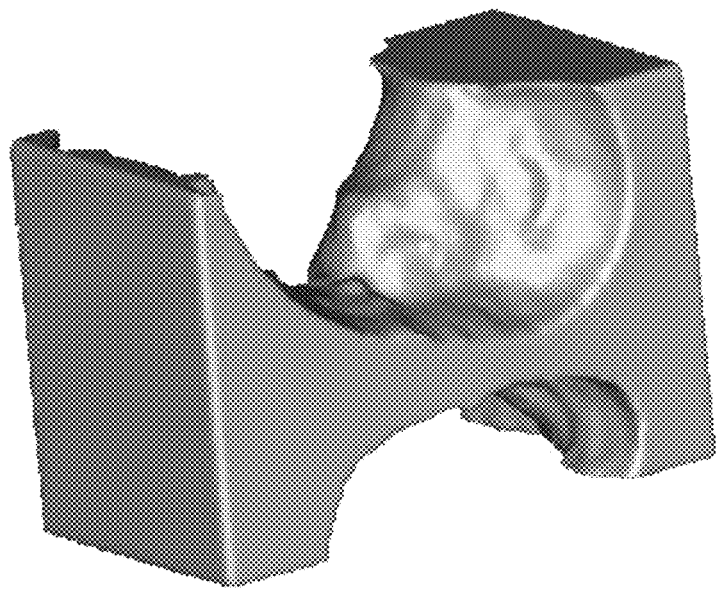
Figure 5:
FIGS. 5(a) and (b) depict the contours of the face of the bone. In 5(a), a block of reverse contour of femoral face was generated allowing in 5(b) the generation of the face contour of the femoral ACL attachment point.
Figure 5:
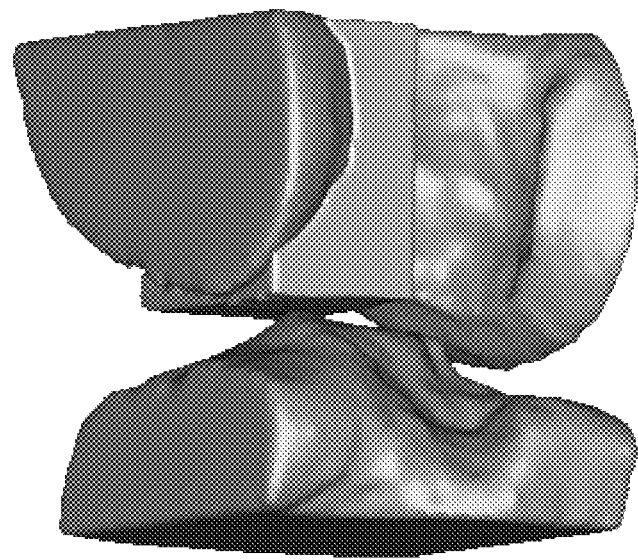
Figure 6:
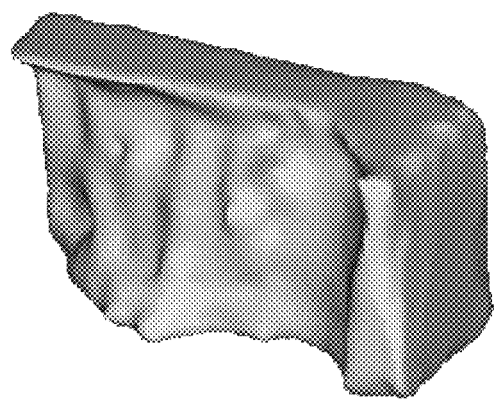
FIGS. 6(a) and (b) depict the ligament attachment point. In 6(a), a block of reverse contour of femoral face permits imaging the ACL's tibial attachment point. Similarly, in 6(b) the face contour of the tibial ACL attachment point is imaged.
Figure 6:
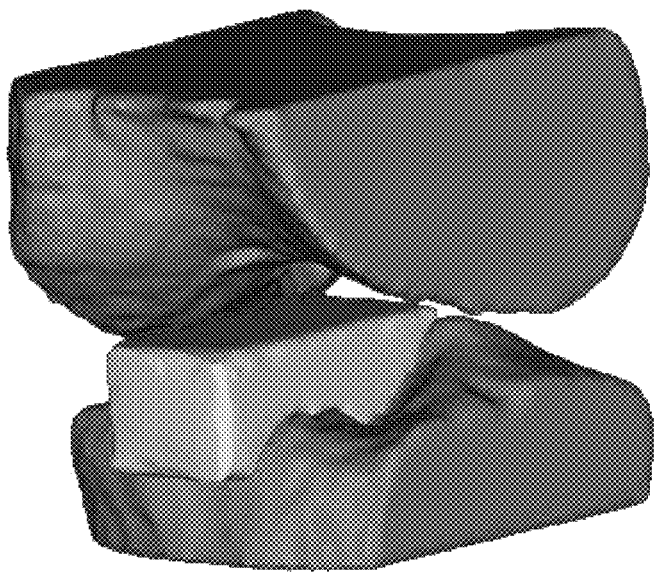

The two masks are cropped to highlight only the area of interest (the attachment points of the ligament), as seen in FIG. 3(a). The holes between the two masks are filled in and the edges are visually verified, generating a new mask seen in FIG. 3(b). A three-dimensional image of the highlighted area is computer generated, representing the surrounding bone (femur and the tibia in the provided Figures), seen in FIG. 4(a). A Boolean extraction is performed on the image, creating the reverse three-dimensional image of the bone so that the contour of the bone can be obtained, seen in FIG. 4(b). The reverse three-dimensional image is sliced, allowing access to the face's contour, seen in FIGS. 5(a) and 6(a). As shown in FIGS. 5(b), this allows visualization of the medial surface of the lateral condyle of the distal end of the femur and the proximal attachment point of the ACL on the face of the bone. A reverse template is then created from the sliced reverse three-dimensional image of the area of where the ACL's true anatomical location is supposed to naturally lie and conforms to the bone contours as the sliced images do, see FIGS. 5(b) and 6(b).

Figure 7:
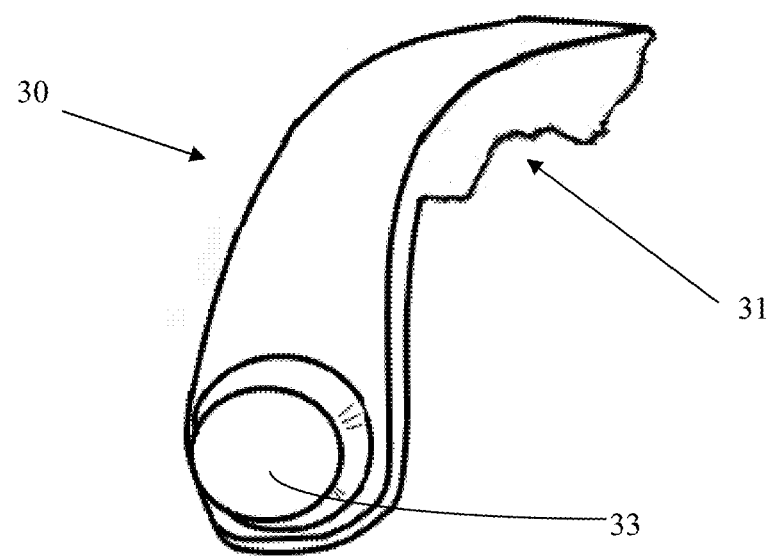
FIG. 7 depicts a certain embodiment of the manufactured surgical guide.

The surgical guide is manufactured from the reverse template. The contours of the bone present on the reverse template remain while a tooling guide is created at the ligament attachment point. The resulting surgical guide is a perfect match to the patient's bone contours and ligament attachment point. The type of tooling guide may be unique to the surgery that is to be performed. Additionally, the surgical guide is preferably developed to fit in the interstitial space between the two bones making up the joint to be addressed in the surgery and has guide cutouts to permit proper rescission of bone (tibial and femoral cores), as seen in FIG. 7.

Similarly, this process would be used to obtain information on the distal attachment point of the ACL that has been exemplified in the Figures. The front of the medial and lateral intercondylar tubercal on the tibia and behind anterior intercondylar area would be analyzed, as before, to generate the ACL's distal attachment point and bone contours, seen in FIGS. 6(a) and (b).

The necessity of the precision of the surgical guide is exemplified based on the understanding that in knee surgery the ligament that joins the femur to the tibia should be placed in such a way that it respects an isometry constraint. The surgical guide allows the surgeon to ensure that the isometry constraint is respected, within a pre-specified tolerance, by locating precise surgical sites. The process of the present invention enables the production of such a precise surgical guide.

Furthermore, three-dimensional models of the ligament attachment sites may be sent to a three dimensional printer to produce a prototype of the face of the model. A three-dimensional model allows the surgeon to verify that the surgical guide is an exact match and prepare for surgery with a more life-like representation of the patient's joint than would be offered from a set of images. The printer maintains accuracy to −0.01 mm, thus maintaining the level of resolution of the created model. The ACL face models are versatile, for example tooled to insert specific guides for known surgical ACL attachment devices. Other uses for the models may be envisioned by one of skill in the art. Furthermore, a placement guide may be optionally added to the surgical guide.

Example: ACL Ligament Reconstruction

The skin surrounding the knee is retracted, and conventional surgical procedures used to excise a semitendinosus tendon, and, if desired, the accompanying gracilis. Alternatively, other ligament replacement materials may be substituted for use in the composite graft of the invention. The soft tissue surrounding the joint is resected or retracted to expose to the bony anatomy of the femur and tibia. The bony joint anatomy may be prepared by removing as much soft tissue around the femur and tibia as needed to allow for good exposure and optimal positioning and registration of the surgical guide.

Figure 8:
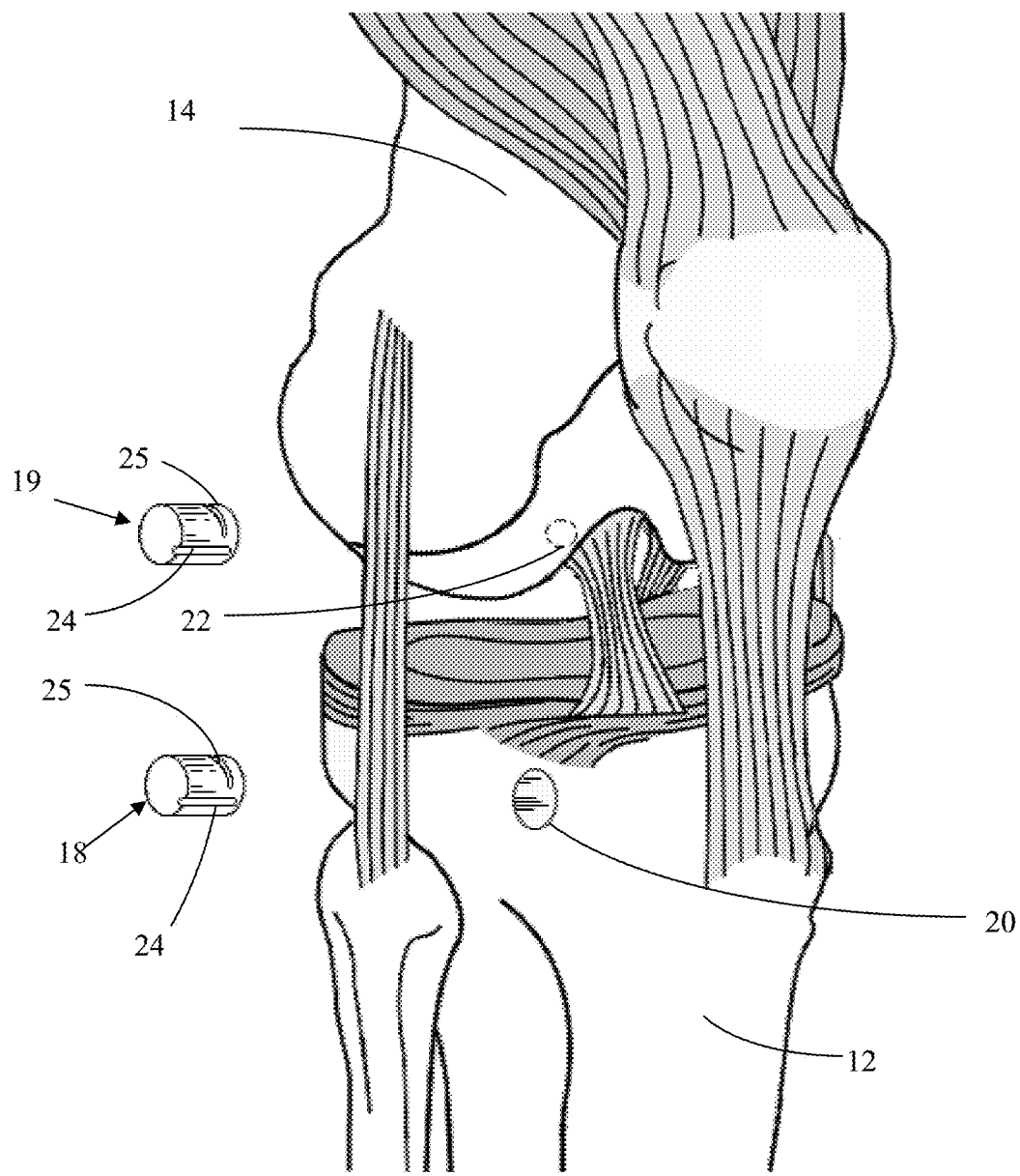
FIG. 8 depicts a knee joint having two bone plugs created from coring out the patient's bone.

The two major bones that meet at the knee joint 10 are tibia 12 and the femur 14, seen in FIG. 8. Tibial bone tunnel 20 is drilled through tibia 12 and femoral bone tunnel 22 through femur 14. Tibial bone tunnel 20 and femoral bone tunnel 22 may be formed using an awl, drill, osteotome, dental hatchet, burr, or other device known in the art, such as a coring reamer. The reamer drills out a core of bone through each of the bone tunnels, forming tibial bone core 18 and femoral bone core 19, which can be used as a bone plug in the composite graft that will be replaced when reconstructing the ligament. The surgical guide is particularly useful in coring, as it locates the drill location without need of a guide pin, which would form a stress riser in the bone plug making the bone plug subject to fracture. Further, the surgical guide properly places the drill location to ensure isometry of the reconstruction.

Figure 9:
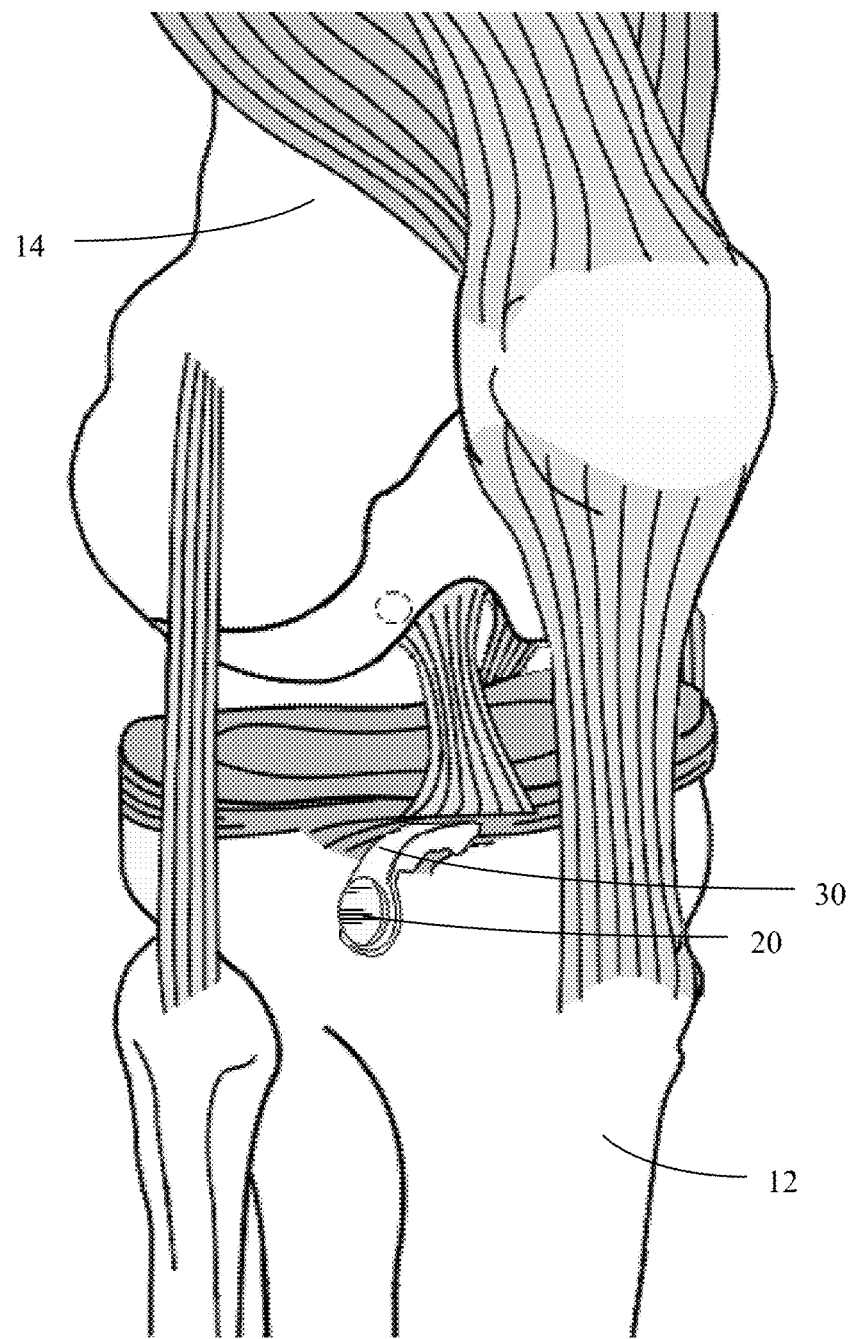
FIG. 9 depicts a certain embodiment of the surgical guide fitted to the patient's bone.

Surgical guide 30 is fitted into the joint, as seen in FIG. 9. The inverse joint contour 31 of surgical guide 30 is custom fit to the contours of the bone articulation, such as the epiphysis of the tibia and fibula, seen in FIG. 7. Guide cut out 32 or drill opening 33 in surgical guide 30 is disposed on pre-determined drilling locations and serves to guide a coring reamer 40 or other drill inserted therethrough. With the patient's leg held fixed, the guide can be used for drilling both the tibial tunnel and then the femoral tunnel. Therefore, a portal for the drill is not required behind the femur and a closed tunnel can be drilled. Both tunnels are drilled through the tibia from the anteromedial tibial incision. The bone cores from the reamer are removed and deburring and debridement procedures undertaken, as is known in the art.

If cores have been drilled out from the bone tunnels they may be used for the bone plugs otherwise, donor bone, namely allograft bone, can be used to make the bone plugs. Referring back to FIG. 8, regardless of the bone plug used, two longitudinal substantially parallel grooves 24 are drilled on opposite sides of each bone plug. As shown in FIG. 9, surgical guide 30 may have groove tracks allowing precise placement of the grooves. The grooves provide a recess in which the semitendinosus tendon 16 and gracilis 17 can be seated. Notch 25 may also be drilled, if desired, across one end of the bone plug so that the tendon can be wrapped alongside and around the end of the bone plug, without protruding excessively from the plug. Notch 25 is not required because the bone tunnel is open at each end providing no restriction on the tendon projecting above the end of the graft.

In some embodiments, suture holes (not shown) are provided in the bone plug, allowing attachment of the tendon to the plug. The suture holes are drilled into the grooves radially through the bone plug and from one of the substantially parallel grooves 24 to the other.

Figure 10:
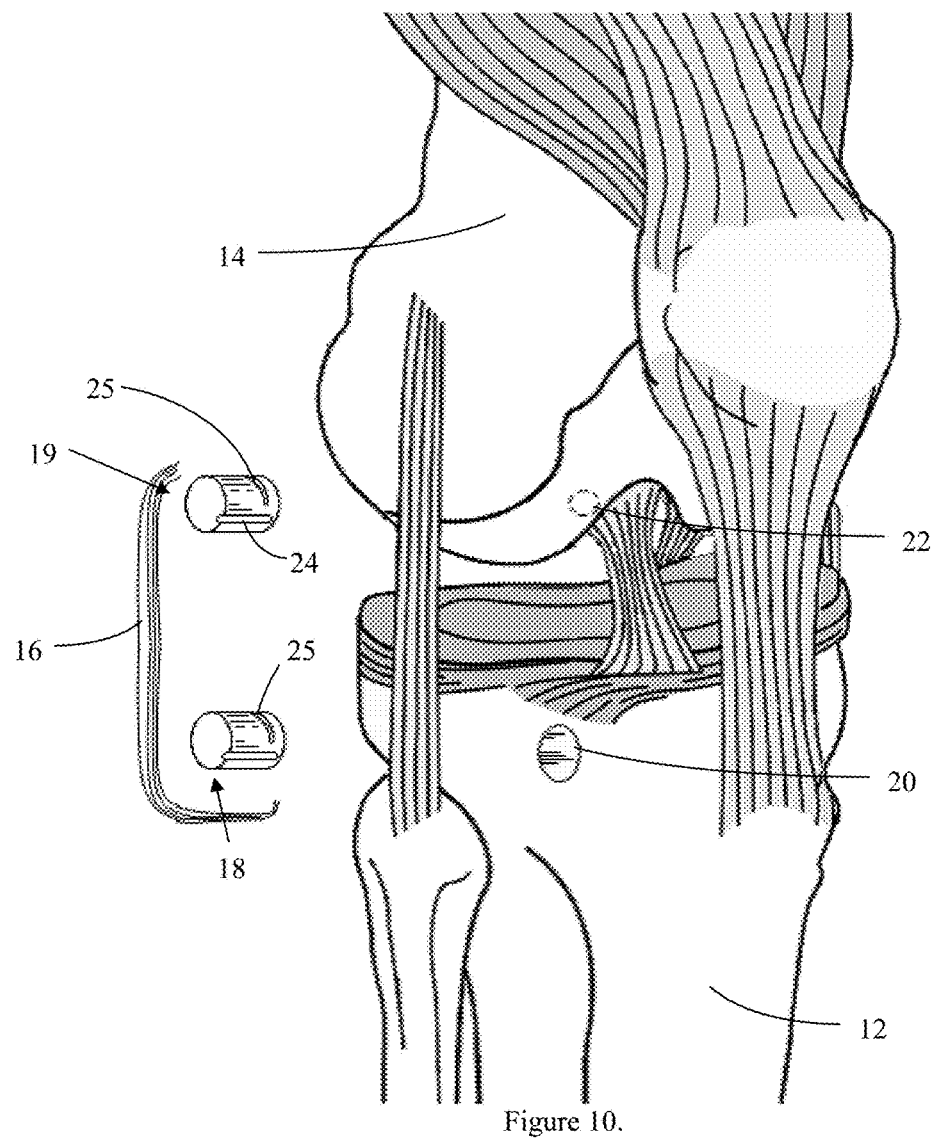
FIG. 10 depicts a patient's joint prior to assembly of the bone plugs and the replacement ligament.
Figure 11:
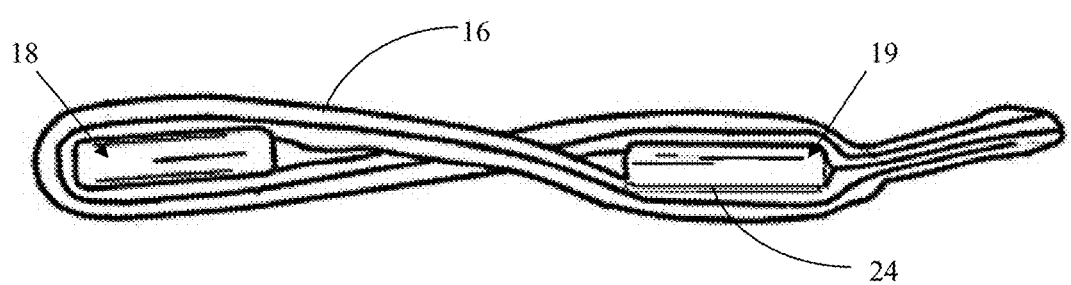
FIG. 11 depicts the bone plugs attached to the replacement ligament.

The semitendinosus tendon 16 and/or gracilis 17 is extended between tibial bone core 18 and femoral bone core 19. The tendons are seated inside the two substantially parallel grooves 24, and about an end of each bone plug, seen in FIG. 10. The tendons are sutured to themselves to form a double loop as shown in FIG. 11. Sutures would also be used through the suture holes to attach the tendon to each of the bone plugs. The tendon strands may be straight or twisted between the bone plugs. Twisting will shorten the length of the graft. A ligament replacement of an embodiment of the invention may include both the semitendinosus tendon and the graeilis. As such four strands will connect the two bone plugs. Other embodiments of the invention may use one or the other of the semitendinosus tendon and gracilis. Still further embodiments of the invention may substitute or combine man-made or artificial fibers or human tissue for the tendons for use as the ligament replacement. The graft is then fixed as is known in the art, such as by fixation using a headless cannulated interference screw.

While this operation has been discussed in terms of using autogenous bone cores, alternative sources of bone plugs may be substituted. Allografts, in which donor bone is freeze-dried or fresh frozen for preservation, are one alternative. The freeze drying process kills cells in the bone and may reduce the risk of transmission of infection.

Another alternative bone plug is the use of synthetic graft material. With any of these alternatives, the bone plugs may be shaped to appear as described above for the autogenous graft. With the allograft and the synthetic graft, the coring reamer is no longer required and an ordinary drill may be used instead for drilling the bone tunnels.

Glossary of Claim Terms

Imaging: is a method or mechanism by which a diagnostic image of a joint is obtained. Including but not limited to the use of static magnetic fields produced via radiofrequency pulse, x-ray radiation, or administration of a chemical entity that alters an anatomical structure allow for diagnostic image. Non-limiting examples of mechanisms include magnetic resonance imaging (MRI), nuclear magnetic resonance imaging (NMRI), computed axial tomography (CAT or CT scan) scan, ultrasound, fluoroscopy, x-ray, tomodensimetric (TDM), positron emission tomography (PET), and combinations thereof.

Ligament attachment point: is a point where a ligament would naturally attach to a bone.

Ligament: is a band of fibrous connective tissue connecting bones to other bones to form a joint.

Mask: is a pixel filter.

RAX Orientation: is an axial orientation with respect to the scanner.

Reverse Image: is an inverse image.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of creating a surgical guide, comprising the steps of:
    imaging a patient's joint;
    collecting a set of images of the patient's joint;
    generating a first mask on each image in the set of images;
    processing the first mask to remove artifacts;
    generating a second mask on each image in the set of images;
    processing the second mask to remove artifacts;
    merging the first and second masks creating a merged mask;
    generating a third mask by filling in any holes in the merged mask;
    creating a three dimensional image of the third mask;
    generating a reverse image of the three dimensional image of the third mask;
    creating a template from the reverse image; and
    manufacturing a surgical guide from the template.

2. The method of claim 1, wherein the surgical guide further includes:
    a body having a first end, a second end, a contacting surface, and a top surface;
    a tooling guide disposed near the second end and at a ligament attachment point;
    the first end adapted to fit in an interstitial space between a set of bones in the joint; and
    the contacting surface inversely contoured to a shape of the patient's joint anatomy.

3. The method of claim 2, wherein the tooling guide is selected from a group consisting of a guide cut out, drill guide, and groove tracks.

4. The method of claim 2, wherein the tooling guide is adapted to accept a tool selected from a group consisting of an awl, drill, osteotome, dental hatchet, burr, and coring reamer.

5. The method of claim 1, further including a step of cropping the merged mask to highlight an attachment point of a ligament.

6. The method of claim 1, wherein the images being collected have an image slice thickness of 0.499998 mm and patient image orientation of RAX.

7. The method of claim 1, wherein the imaging is accomplished using an MIll with a magnetic field strength of 3 tesla.

8. The method of claim 1, wherein the images are collected at an image resolution of 512 pixels by 512 pixels and a pixel size of 0.4688 mm.

9. The method of claim 1, wherein the first mask filters pixels that are within a contrast range of 0 to 800.

10. The method of claim 1, wherein the second mask filters pixels that are within a contrast range of 1250 to 4000.

11. The method of claim 1, further comprising transferring the three dimensional image to a three dimensional printer to generate a model.

12. A method of creating a surgical guide, comprising the steps of:
    imaging a patient's joint;
    collecting a set of images of the patient's joint;
    generating a first mask on the set of images, wherein the first mask filters pixels that are within a contrast range of 0 to 800;
    processing the first mask to remove artifacts;
    generating a second mask on the set of images, wherein the second mask filters pixels that are within a contrast range of 1250 to 4000;
    processing the second mask to remove artifacts;
    merging the first and second masks creating a merged mask;
    generating a third mask by filling in any holes in the merged mask;
    creating a three dimensional image of the third mask;
    generating a reverse image of the three dimensional image of the third mask;
    creating a template from the reverse image; and
    manufacturing a surgical guide from the template.

13. The method of claim 12, wherein the surgical guide further includes:
    a body having a first end, a second end, a contacting surface, and a top surface;
    a tooling guide disposed near the second end and at ad ligament attachment point;
    the first end adapted to fit in an interstitial space between a set of bones in the joint; and
    the contacting surface inversely contoured to a shape of the patient's joint anatomy.

14. The method of claim 13, wherein the tooling guide is selected from a group consisting of a guide cut out, drill guide, and groove tracks.

15. The method of claim 13, wherein the tooling guide is adapted to accept a tool selected from a group consisting of an awl, drill, osteotome, dental hatchet, burr, and coring reamer.

16. The method of claim 12, further including a step of cropping the merged mask to highlight an attachment point of a ligament.

17. The method of claim 12, wherein the images being collected have an image slice thickness of 0.499998 mm and patient image orientation of RAX.

18. The method of claim 12, wherein the imaging is accomplished using an MRI with a magnetic field strength of 3 tesla.

19. The method of claim 12, wherein the images are collected at an image resolution of 512 pixels by 512 pixels and a pixel size of 0.4688 mm.

20. The method of claim 12, further comprising transferring the three dimensional image to a three dimensional printer to generate a model.

* * * * *

UNITED STATES PATENT AND TRADEMARK OFFICE
CERTIFICATE OF CORRECTION

PATENT NO. : 9,700,259 B1  
APPLICATION NO. : 14/287987  
DATED : July 11, 2017  
INVENTOR(S) : Charles Nofsinger Page 1 of 1

It is certified that error appears in the above-identified patent and that said Letters Patent is hereby corrected as shown below:

In the Claims

Column 9, Claim 7, Line 48 should read:
plished using an MRI with a magnetic field strength of 3

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*